US012644825B2

(12) United States Patent
Wan et al.

(10) Patent No.: US 12,644,825 B2
(45) Date of Patent: Jun. 2, 2026

(54) SIMULTANEOUS DETECTION METHOD AND SYSTEM FOR DISSOLVED GAS AND PARTIAL DISCHARGE IN INSULATING OIL

(71) Applicants:Chongqing University, Chongqing (CN); State Grid Chongqing Electric Power Research Institute, Chongqing (CN); Shandong Taikai Transformer Co., Ltd, Tai'an (CN); Optosky (Xiamen) Optical Ltd, Xiamen (CN)

(72) Inventors: Fu Wan, Chongqing (CN); Weigen Chen, Chongqing (CN); Zhiyi Luo, Chongqing (CN); Yingkai Long, Chongqing (CN); Pinyi Wang, Chongqing (CN); Lin Du, Chongqing (CN); Qiuxia Sun, Tai'an (CN); Quan Zhou, Chongqing (CN); Youyuan Wang, Chongqing (CN); Hongfei Liu, Xiamen (CN)

(73) Assignees: Chongqing University, Chongqing (CN); State Grid Chongqing Electric power Research Institute, Chongqing (CN); Shandong Taikai Transformer Co., Ltd., Tai'an (CN); Optosky (Xiamen) Optical Ltd., Xiamen (CN)

( * ) Notice: Subject to any disclaimer, the term of this patent is extended or adjusted under 35 U.S.C. 154(b) by 289 days.

(21) Appl. No.: 18/543,861

(22) Filed: Dec. 18, 2023

(65) Prior Publication Data
US 2024/0288359 A1    Aug. 29, 2024

(30) Foreign Application Priority Data
Feb. 28, 2023    (CN) .......................... 202310180891.2

(51) Int. Cl.
*G01N 21/17* (2006.01)
*G01N 21/27* (2006.01)
(Continued)

(52) U.S. Cl.
CPC ......... *G01N 21/1702* (2013.01); *G01N 21/27* (2013.01); *G01N 21/45* (2013.01);
(Continued)

(58) Field of Classification Search
CPC ..... G01N 2021/1704; G01N 2021/458; G01N 21/1702; G01N 21/27; G01N 21/45;
(Continued)

(56) References Cited

U.S. PATENT DOCUMENTS

2012/0291521 A1* 11/2012 Cavallini .......... G01N 33/2841
73/19.1

FOREIGN PATENT DOCUMENTS

CN      102323527 A  *  1/2012  ............. G01R 31/12
CN      108195729 A  *  6/2018  ............. G01N 15/06
(Continued)

OTHER PUBLICATIONS

Chen et al, Highly Sensitive Optical Fiber Photoacoustic Sensor for In Situ Detection of Dissolved Gas in Oil, IEEE Transactions on Instrumentation and Measurement, vol. 70, 2021 (Year: 2021).*
(Continued)

*Primary Examiner* — David L Singer

(57)    ABSTRACT

There is provided a simultaneous detection method and system for dissolved gas and partial discharge in insulating oil, and belongs to the field of electrical devices. The method includes the steps: freely diffusing the dissolved gas in the insulating oil to an Fabry-Perot (F-P) optical fiber interference cavity through an oil-gas separation membrane; coupling pump light and probe light into the F-P optical fiber interference cavity through a frequency division multi-
(Continued)

plexer; making, by an optoacoustic effect of the dissolved gas stimulated by the pump light and an ultrasonic wave generated by the partial discharge, the oil-gas separation membrane vibrate; detecting, by the probe light, vibration of the oil-gas separation membrane, which changes a cavity length, wherein when the probe light is reflected by the oil-gas separation membrane, an interference signal is generated due to the change of the cavity length.

15 Claims, 2 Drawing Sheets

(51) Int. Cl.
  *G01N 21/45*          (2006.01)
  *G01N 33/28*          (2006.01)
  *G01R 31/12*          (2020.01)
(52) U.S. Cl.
  CPC ..... *G01N 33/2841* (2013.01); *G01R 31/1218* (2013.01); *G01R 31/1281* (2013.01); *G01N 2021/1704* (2013.01); *G01N 2021/458* (2013.01); *G01N 2201/06113* (2013.01)
(58) Field of Classification Search
  CPC ..... G01N 2201/06113; G01N 33/2841; G01R 31/1209; G01R 31/1218; G01R 31/1227; G01R 31/1281
  See application file for complete search history.

(56) References Cited

FOREIGN PATENT DOCUMENTS

| | | | | | |
|---|---|---|---|---|---|
| CN | 109387759 | A | * | 2/2019 | ............. G01H 9/004 |
| CN | 109490731 | A | * | 3/2019 | ......... G01R 31/1218 |
| CN | 109799435 | A | * | 5/2019 | ............. G01R 31/12 |
| CN | 110542839 | A | * | 12/2019 | ......... G01R 31/1281 |
| CN | 110823809 | A | * | 2/2020 | ............. G01N 21/01 |
| CN | 111289851 | A | * | 6/2020 | ......... G01R 31/1218 |
| CN | 111854923 | A | * | 10/2020 | ............. G01H 9/004 |
| CN | 112665647 | A | * | 4/2021 | ............. G01D 21/02 |
| CN | 113567818 | A | * | 10/2021 | ......... G01R 31/1218 |
| CN | 113567819 | A | * | 10/2021 | ......... G01R 31/1218 |
| CN | 113589113 | A | * | 11/2021 | ......... G01R 31/1218 |
| CN | 113589114 | A | * | 11/2021 | ......... G01R 31/1218 |
| CN | 115266600 | A | * | 11/2022 | ......... G01N 21/1702 |

OTHER PUBLICATIONS

Jiang et al, Optical Sensing in Power Transformers, 2021 JohnWiley & Sons Ltd., Chapter 5 Partial Discharge Detection with Optical Methods (Year: 2021).*
Yang et al, Detection of Dissolved Gas in Transformer Oil Based on All-Optical Photoacoustic Spectroscopy, IEEE, 2020 (Year: 2020).*

* cited by examiner

Figure 2:
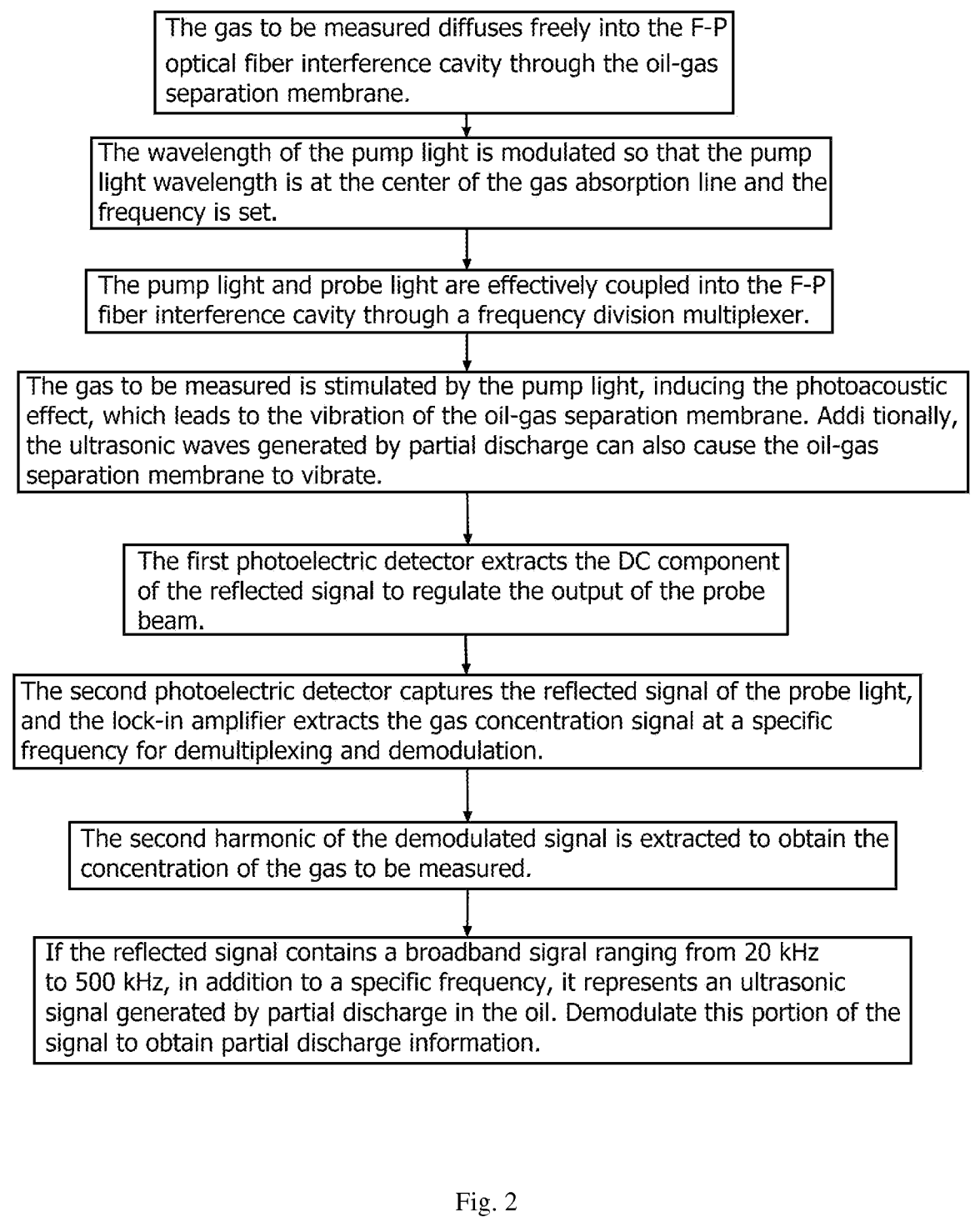

The gas to be measured diffuses freely into the F-P optical fiber interference cavity through the oil-gas separation membrane.

↓

The wavelength of the pump light is modulated so that the pump light wavelength is at the center of the gas absorption line and the frequency is set.

↓

The pump light and probe light are effectively coupled into the F-P fiber interference cavity through a frequency division multiplexer.

↓

The gas to be measured is stimulated by the pump light, inducing the photoacoustic effect, which leads to the vibration of the oil-gas separation membrane. Addi tionally, the ultrasonic waves generated by partial discharge can also cause the oil-gas separation membrane to vibrate.

↓

The first photoelectric detector extracts the DC component of the reflected signal to regulate the output of the probe beam.

↓

The second photoelectric detector captures the reflected signal of the probe light, and the lock-in amplifier extracts the gas concentration signal at a specific frequency for demultiplexing and demodulation.

↓

The second harmonic of the demodulated signal is extracted to obtain the concentration of the gas to be measured.

↓

If the reflected signal contains a broadband sigral ranging from 20 kHz to 500 kHz, in addition to a specific frequency, it represents an ultrasonic signal generated by partial discharge in the oil. Demodulate this portion of the signal to obtain partial discharge information.

SIMULTANEOUS DETECTION METHOD AND SYSTEM FOR DISSOLVED GAS AND PARTIAL DISCHARGE IN INSULATING OIL

CROSS-REFERENCE TO RELATED APPLICATION

This application claims priority from the Chinese patent application 202310180891.2 filed Feb. 28, 2023, the content of which is incorporated herein in the entirety by reference.

TECHNICAL FIELD

The present disclosure belongs to the field of electrical devices, and relates to operation state parameter detection of an oil-immersed electrical device, in particular to a simultaneous detection method and system for dissolved gas and partial discharge in insulating oil.

BACKGROUND

A healthy insulation state is the key to ensure safe operation of a power transformer, partial discharge is an early sign of insulation degradation of the power transformer, and when an electrical device is under an action of high voltage, heat and other factors for a long time, gradual development of insulation aging damage inside the device will lead to a significant decline in insulation performance, which becomes a hidden danger for the reliable operation of a power transformation device, but also an important source of endangering operation safety of a power grid. It is found from an investigation report of a power grid accident that a proportion of insulation faults in faults of the electrical device is 50% or above, and the higher the voltage level, the greater the occurrence probability of the insulation faults. The primary culprits behind insulation accidents are partial discharges. Partial discharge is an early indication that the insulation performance of large-scale power equipment is starting to deteriorate. If left unchecked, its progressive development can lead to insulation breakdown and result in power accidents. In addition, when the oil-immersed transformer is in a normal operation state, its insulating oil will gradually age and deteriorate under the action of heat and electricity, and decompose a very small amount of gas (main components are hydrogen, methane, ethane, ethylene, acetylene, carbon monoxide, carbon dioxide, etc.), when an overheating fault, a partial discharge fault or internal insulation moisture occurs in the transformer, this decomposition will be strengthened, and produced gas will be increased dramatically.

Therefore, the detection of fault characteristic gases in transformers exhibits remarkable sensitivity and effectiveness in early diagnosis and evaluating the progression of latent faults. Currently, mainstream gas detection methods encompass gas chromatography, nanomaterial gas sensing, fiber Bragg grating, Raman spectroscopy, laser absorption spectroscopy, and photoacoustic spectroscopy, etc. The detection of partial discharge in transformers serves to anticipate and identify insulation deficiencies, thereby preventing potential latent and sudden accidents. Commonly employed methods for partial discharge detection include the pulse current method, ultra-high frequency method, and ultrasonic method, among others.

Single detection for characteristic gas or partial discharge cannot fully grasp an operation health state of the oil-immersed transformer, so an integrated detection method for characteristic gas and partial discharge is proposed, which is of great significance to ensure the safe and stable operation of the transformer.

SUMMARY

In view of this, the present disclosure aims to provide an integrated detection method and system for dissolved gas and partial discharge in insulating oil of an oil-immersed transformer. This system can simultaneously detect information regarding characteristic gas and partial discharge, allowing for a comprehensive assessment of the transformer's operational state.

In order to achieve the above objective, the present disclosure provides the following technical solutions:

Scheme 1, a simultaneous detection method for dissolved gas and partial discharge in insulating oil, includes the following steps:

S1, freely diffusing the dissolved gas in the insulating oil to an F-P optical fiber interference cavity 6 through an oil-gas separation membrane 17;

S2, coupling pump light and probe light into the F-P optical fiber interference cavity 6 through a frequency division multiplexer 5;

S3, making, by an optoacoustic effect of the dissolved gas stimulated by the pump light and an ultrasonic wave generated by the partial discharge, the oil-gas separation membrane 17 vibrate;

S4, detecting, by the probe light, vibration of the oil-gas separation membrane, which changes a cavity length, wherein when the probe light is reflected by the oil-gas separation membrane 17, the interference signal is generated due to the change of the cavity length, and then receiving the interference signal by the photoelectric detector; and S5, obtaining information of the dissolved gas and the partial discharge in the insulating oil by processing and analyzing the interference signal.

Preferably, the pump light is periodically modulated light generated by a distributed feedback (DFB) semiconductor laser, with a wavelength corresponding to the center of a dissolved gas absorption line, and its frequency does not exceed 20 kHz. The probe light is continuous light generated by the DFB semiconductor laser. Using an optical switch 18, the pump light of different wavelengths is controlled to enter the F-P optical fiber interference cavity 6 in sequence to conduct multi-component gas detection.

Furthermore, in step S4, a direct-current component of the interference signal is extracted through a first photoelectric detector 13, the direct-current component is processed by a low-pass filter 12 and transmitted to a servo controller 11, and the servo controller 11 controls a probe light generator 7 to work at an orthogonal working point of an FPI.

Further, in steps S4 and S5, the interference signal is received by a second photoelectric detector 14. Then, an interference signal of a specific frequency is extracted by a lock-in amplifier 15. Subsequently, the interference signal of the specific frequency is demultiplexed and demodulated to obtain a second harmonic of a gas photoacoustic signal, from which the concentration information of the dissolved gas is obtained.

Furthermore, a broadband interference signal ranging from 20 kHz to 500 kHz is extracted in the frequency domain of the interference signal by the computer 16. The frequency and intensity information of the partial discharge is then obtained through demultiplexing and demodulating.

Scheme 2, a simultaneous detection system for dissolved gas and partial discharge in insulating oil, includes a pump light generator 3, a frequency division multiplexer 5, an F-P optical fiber interference cavity 6, a probe light generator 7, a circulator 8, a filter 9, a low-pass filter 12, a second photoelectric detector 14, a lock-in amplifier 15, a computer 16, and an oil-gas separation membrane 17.

The pump light generator 3, the frequency division multiplexer 5 and the F-P optical fiber interference cavity 6 are successively connected; the oil-gas separation membrane 17 is arranged in the F-P optical fiber interference cavity 6; the circulator 8 is respectively connected with the probe light generator 7, the frequency division multiplexer 5 and the filter 9; and the filter 9 is successively connected with the second photoelectric detector 14, the lock-in amplifier 15 and the computer 16.

Optionally, the system further includes a function generator 1, a laser controller 2, a laser power amplifier 4, an optical fiber coupler 10, a servo controller 11, the low-pass filter 12, the first photoelectric detector 13 and an optical switch 18.

The laser controller 2 is respectively connected with the function generator 1, the lock-in amplifier 15 and the pump light generator 3; the optical switch 18 and the laser power amplifier 4 are arranged between the pump light generator 3 and the frequency division multiplexer 5; the optical fiber coupler 10 is respectively connected with the filter 9, the first photoelectric detector 13 and the second photoelectric detector 14; and the first photoelectric detector 13, the low-pass filter 12, the servo controller 11 and the probe light generator 7 are successively connected.

The present disclosure has the beneficial effects: the present disclosure adopts an optical fiber photoacoustic spectrometry technology to simultaneously detect the relevant information of the characteristic gas in the transformer insulating oil and the partial discharge, thereby reducing the detection cost, and realizing the multi-parameter integrated accurate evaluation of the transformer device state.

An oil-immersed transformer insulation fault multi-parameter online monitoring system provided by the present disclosure can conduct in-situ real-time online monitoring of the fault decomposition gases and partial discharges in the oil-immersed transformer, enabling qualitative and quantitative assessment of the insulation faults. The fault online monitoring system adopts all-fiber signal transmission, which possesses advantages such as robust resistance to electromagnetic interference, high precision, no requirement for carrier gas consumption, and minimal maintenance in the later stages.

BRIEF DESCRIPTION OF FIGURES

In order to make the objectives, technical solutions and advantages of the present disclosure clearer, the present disclosure will be described in detail preferably with reference to the accompanying drawings, where:

FIG. 2 is a schematic diagram of steps of a detection method of the present disclosure.

Figure 1:
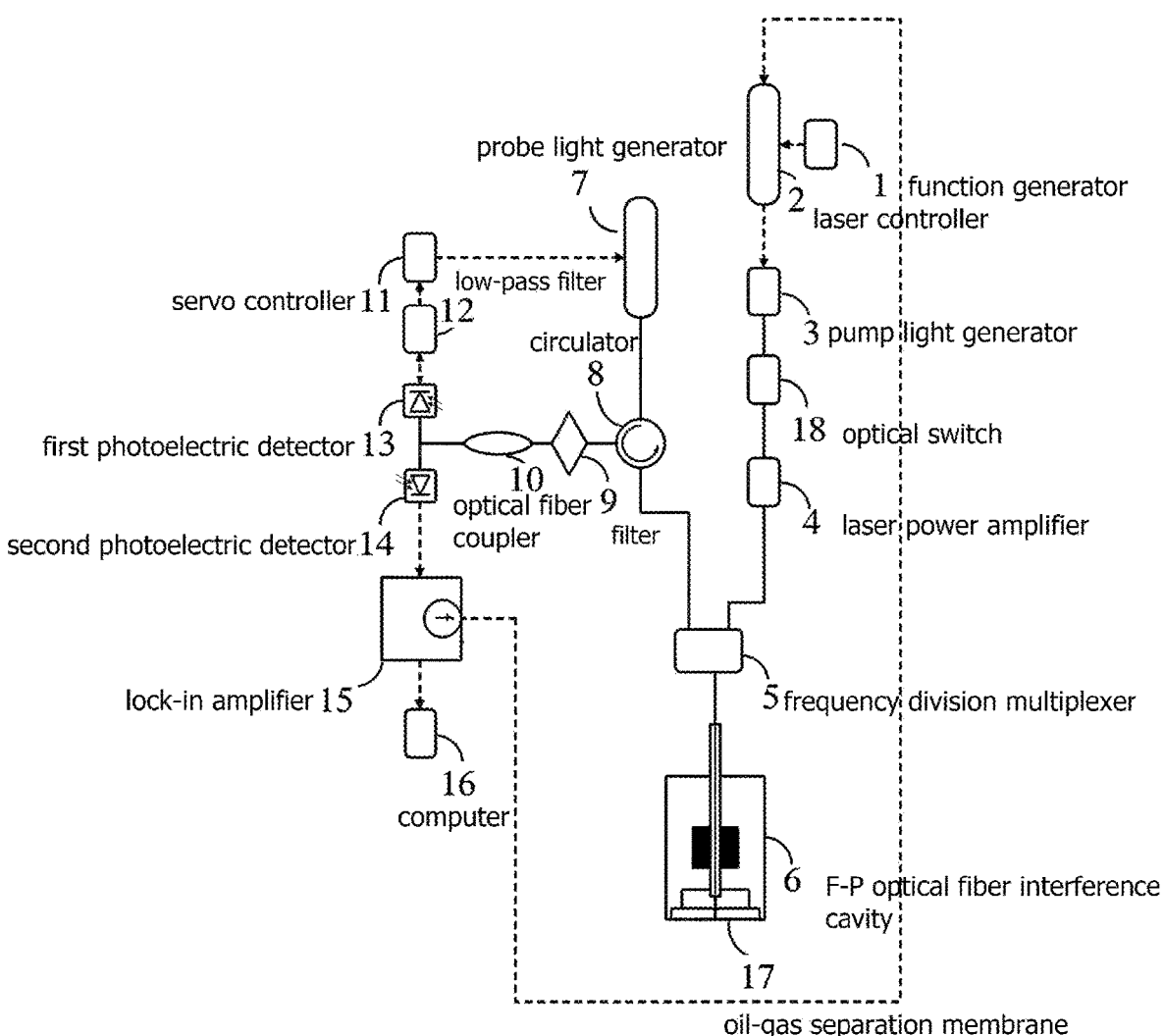
FIG. 1 is a schematic structural diagram of a detection system of the present disclosure.

Reference signs of the accompanying drawings: 1—function generator; 2—laser controller; 3—pump light generator; 4—laser power amplifier; 5—frequency division multiplexer; 6-F-P optical fiber interference cavity; 7—probe light generator; 8—circulator; 9—filter; 10—optical fiber coupler; 11—servo controller; 12—low—pass filter; 13—first photoelectric detector; 14—second photoelectric detector; 15—lock—in amplifier; 16—computer; 17—oil—gas separation membrane; and 18—optical switch.

DETAILED DESCRIPTION

Implementations of the present disclosure are illustrated below through specific concrete examples, and those skilled in the art may easily understand other advantages and functions of the present disclosure from the contents disclosed in this specification. The present disclosure may also be implemented or applied in other different specific implementations, and various details in this specification may also be modified or changed based on different points of view and applications without deviating from the spirit of the present disclosure. It should be noted that diagram forms provided in the following embodiments illustrate the basic concepts of the present disclosure only in a schematic mode, and the following embodiments and the features in the embodiments may be combined with each other without conflict.

The accompanying drawings are for exemplarily illustrative only, only show schematic diagrams, not physical diagrams, and cannot be construed as limitations to the present disclosure; in order to better illustrate the embodiments of the present disclosure, some parts in the accompanying drawings will be omitted, enlarged or narrowed, which does not represent the size of the actual product; and for those skilled in the art, it is understandable that certain well-known structures in the accompanying drawings and their descriptions may be omitted.

The same or similar reference signs in the accompanying drawings of the embodiments of the present disclosure correspond to the same or similar components; in the description of the present disclosure, it is to be understood that if the terms "up", "down", "left", "right", "front", "back", etc. indicate an orientation or position relationship based on an orientation or position relationship shown in the accompanying drawings, it is only for the purpose of facilitating the description of the present disclosure and simplifying the description, rather than indicating or implying that an apparatus or element referred to must have a specific orientation, and be constructed and operated in the specific orientation, therefore, the terms describing the position relationship in the accompanying drawings are for exemplary illustration only and cannot be understood as a limitation to the present disclosure, and the specific meaning of the above terms may be understood by those ordinarily skilled in the art according to the specific circumstances.

FIG. 1 shows a connection structure of a simultaneous detection system for dissolved gas and partial discharge in insulating oil. The present disclosure considers that an ultrasonic method for measuring partial discharge and a photoacoustic spectrometry method for measuring fault characteristic gas essentially detect acoustic signals, and therefore an optical fiber spectrum photoacoustic technology is adopted to simultaneously detect the characteristic gas and the partial discharge. The detection system includes a function generator 1, laser controller 2, pump light generator 3, laser power amplifier 4, frequency division multiplexer 5, F-P optical fiber interference cavity 6, probe light generator 7, circulator 8, a filter 9, optical fiber coupler 10, servo controller 11, low-pass filter 12, the first photoelectric detector 13, the second photoelectric detector 14, lock-in amplifier 15, computer 16, oil-gas separation membrane 17 and optical switch 18.

The function generator 1 generates a triangular wave scanning signal, which is superimposed with a sinusoidal modulation signal output by the lock-in amplifier 15 to scan a gas absorption line. In other words, the output of the pump light generator 3 undergoes modulation through a wavelength modulation technology. The wavelength of the pump light corresponds to the center of the absorption line of the dissolved gas. The specific frequency of the pump light is set to no more than 20 kHz. The pump light generator may be a DFB semiconductor fiber laser. The light emitted by the pump light generator 3 is controlled by the optical switch 18. This allows the pump light of different wavelengths to enter the frequency division multiplexer 5 after passing through the laser power amplifier 4, which is used to detect gases of different components. In this process, the pump light of different wavelengths enters the F-P fiber interference cavity 6 in batches.

The probe light generator 7 outputs probe light, and the probe light passes through the circulator 8 and enters the frequency division multiplexer 5 to be coupled with the pump light, wherein the probe light generator may adopt a DFB semiconductor laser. The probe light generator 7 will also be controlled by the servo controller 11 to keep the probe light generator 7 work at an orthogonal working point of an FPI.

The probe light and the pump light are combined through the frequency division multiplexer 5 and then enter the F-P fiber interference cavity 6. In the interference cavity, the gas dissolved in the insulating oil is excited to a high energy state by the pump light, causing collision relaxation. This will cause the photoacoustic effect in the gas in the F-P optical fiber interference cavity, resulting in the vibration of the oil-gas separation membrane 17. The frequency of this vibration corresponds to the modulation frequency of the pump light. In addition, the partial discharge will also make the oil-gas separation membrane 17 vibrate, and a vibration frequency is 20 kHz to 500 kHz. The probe light detects the vibration frequency and intensity of the oil-gas separation membrane 17. The vibration of the oil-gas separation membrane will alter the cavity length. This change in cavity length results in the interference signal of the probe light. The interference signal passes through the circulator 8 and then enters the filter 9, where the pump light transmitted with the interference signal is filtered out. Subsequently, the interference signal is simultaneously received by both the first photoelectric detector 13 and the second photoelectric detector 14 after passing through the fiber coupler 10. The first photoelectric detector extracts the DC component of the interference signal, which is then processed by the low-pass filter 12 and transmitted to the servo controller 11. The servo controller controls the probe light generator to operate at the orthogonal working point of the FPI. The second photoelectric detector receives the interference signal, it is then transmitted to the lock-in amplifier 15. The interference signal, which corresponds to the specific frequency for the lock-in amplifier, is demultiplexed and demodulated to obtain the photoacoustic signal. The second harmonic of the photoacoustic signal is extracted to acquire the relevant information regarding gas concentration. On the other hand, the computer 16 extracts the broadband signal ranging from 20 kHz to 500 kHz in the frequency domain of the original signal, and then demultiplexes and demodulates it to obtain the frequency and intensity information of partial discharge.

A simultaneous detection method for dissolved gas and partial discharge in insulating oil of the present disclosure is shown in FIG. 2. The method includes the specific steps:

1. the dissolved gas in the insulating oil is freely diffused to an F-P optical fiber interference cavity 6 through an oil-gas separation membrane 17.

2. Pump light and probe light are coupled into the F-P optical fiber interference cavity 6 through a frequency division multiplexer 5; wherein the pump light is periodically modulated light, and its wavelength is a wavelength corresponding to a center of a dissolved gas absorption line, and its frequency is not greater than 20 kHz. Through an optical switch 18, the pump light of different wavelengths enters the F-P optical fiber interference cavity 6 in batches to achieve multi-component gas detection.

The probe light is continuous light, and is generated by a DFB semiconductor laser.

3. An optoacoustic effect of the dissolved gas stimulated by the pump light and an ultrasonic wave generated by the partial discharge make the oil-gas separation membrane 17 vibrate.

4. The probe light detects the vibration of the oil-gas separation membrane 17, which changes the cavity length, the probe light, when reflected by the oil-gas separation membrane 17, creates an interference signal due to the altered cavity length, this interference signal is received by the photoelectric detector and then is processed and analyzed to obtain information about the dissolved gas in the insulating oil and partial discharge, specifically:

the interference signal is received by a second photoelectric detector 14, then, the interference signal of a specific frequency is extracted by a lock-in amplifier 15 for demultiplexing and demodulation, and the second harmonic of the demodulated signal is extracted to obtain the concentration information of the dissolved gas.

At the same time, the broadband interference signal ranging from 20 kHz to 500 kHz is extracted in the frequency domain of the original signal by the computer 16, and the frequency and intensity information of partial discharge is obtained through demultiplexing and demodulation.

In the process of receiving the interference signal, a direct-current component of the interference signal is extracted by a first photoelectric detector 13, the direct-current component is processed by a low-pass filter 12 and transmitted to a servo controller 11, and the servo controller 11 controls a probe light generator 7 to work at an orthogonal working point of an FPI.

Finally, the above embodiments are used only to illustrate the technical solutions of the present disclosure and not to limit them, and although the present disclosure is described in detail by reference to the preferred embodiments, it should be understood by those ordinarily skilled in the art that the technical solutions of the present disclosure may be modified or equivalently replaced without deviating from the purpose and scope of the technical solutions, and they shall fall within the scope of the claims of the present disclosure.

What is claimed is:

1. A simultaneous detection method for dissolved gas and partial discharge in insulating oil, comprising the following steps:

S1, freely diffusing the dissolved gas in the insulating oil to an Fabry-Perot (F-P) optical fiber interference cavity (6) through an oil-gas separation membrane (17);

S2, coupling pump light and probe light into the F-P optical fiber interference cavity (6) through a frequency division multiplexer (5);

S3, making, by an optoacoustic effect of the dissolved gas stimulated by the pump light and an ultrasonic wave generated by the partial discharge, the oil-gas separation membrane (17) vibrates;

S4, detecting, by the probe light, vibration of the oil-gas separation membrane (17), which changes a cavity length, wherein when the probe light is reflected by the oil-gas separation membrane (17), an interference signal is generated due to the change of the cavity length, and then receiving the interference signal by a photoelectric detector; and S5, obtaining information of the dissolved gas and the partial discharge in the insulating oil by processing and analyzing the interference signal.

2. The detection method according to claim 1, wherein the pump light is periodically modulated light, and a wavelength of the pump light is a wavelength corresponding to a center of a dissolved gas absorption line, and a frequency of the pump light is no more than 20 kHz.

3. The detection method according to claim 2, wherein the pump light of different wavelengths enters the F-P optical fiber interference cavity (6) in batches through an optical switch (18) to achieve multi-component gas detection.

4. The detection method according to claim 1, wherein the probe light is continuous light and generated by a distributed feedback (DFB) semiconductor laser.

5. The detection method according to claim 1, wherein in step S4, a DC component of the interference signal is extracted through a first photoelectric detector (13), the DC component is processed by a low-pass filter (12) and then transmitted to a servo controller (11), and the servo controller (11) controls a probe light generator (7) to operate at an orthogonal working point of an Fabry-Perot Interferometry (FPI).

6. The detection method according to claim 1, wherein in steps S4 and S5, the interference signal is received by a second photoelectric detector (14), then, the interference signal of a specific frequency is extracted by the lock-in amplifier (15), and subsequently, the interference signal of the specific frequency is demultiplexed and demodulated to obtain the second harmonic of a gas photoacoustic signal, from which the concentration information of the dissolved gas is obtained.

7. The detection method according to claim 6, wherein at the same time, a broadband interference signal ranging from 20 kHz to 500 kHz is extracted in a frequency domain of an original signal by a computer (16), and frequency and intensity information of partial discharge is obtained through demultiplexing and demodulation.

8. A simultaneous detection system for dissolved gas and partial discharge in insulating oil applying the detection method according to claim 1, wherein the detection system comprises:

a pump light generator (3);
a frequency division multiplexer (5);
an F-P optical fiber interference cavity (6);
a probe light generator (7);
a circulator (8);
a filter (9);
a low-pass filter (12);
a second photoelectric detector (14);
a lock-in amplifier (15);
a computer (16); and
an oil-gas separation membrane (17);
wherein the pump light generator (3), the frequency division multiplexer (5) and the F-P optical fiber interference cavity (6) are successively connected;

wherein the oil-gas separation membrane (17) is arranged in the F-P optical fiber interference cavity (6);

wherein the circulator (8) is respectively connected with the probe light generator (7), the frequency division multiplexer (5) and the filter (9); and wherein the filter (9) is successively connected with the second photoelectric detector (14), the lock-in amplifier (15) and the computer (16).

9. The detection system according to claim 8, wherein the system further comprises:

a function generator (1);
a laser controller (2);
a laser power amplifier (4);
an optical fiber coupler (10);
a servo controller (11), the low-pass filter (12);
a first photoelectric detector (13) and;
an optical switch (18);

wherein the laser controller (2) is respectively connected with the function generator (1), the lock-in amplifier (15) and the pump light generator (3);

wherein the optical switch (18) and the laser power amplifier (4) are arranged between the pump light generator (3) and the frequency division multiplexer (5); the optical fiber coupler (10) is respectively connected with the filter (9), the first photoelectric detector (13) and the second photoelectric detector (14); and wherein the first photoelectric detector (13), the low-pass filter (12), the servo controller (11) and the probe light generator (7) are successively connected.

10. The simultaneous detection system of claim 8, wherein the pump light is periodically modulated light, and a wavelength of the pump light is a wavelength corresponding to a center of a dissolved gas absorption line, and a frequency of the pump light is no more than 20 kHz.

11. The simultaneous detection system of claim 10, wherein the pump light of different wavelengths enters the F-P optical fiber interference cavity (6) in batches through an optical switch (18) to achieve multi-component gas detection.

12. The simultaneous detection system of claim 8, wherein the probe light is continuous light and generated by a DFB semiconductor laser.

13. The simultaneous detection system of claim 8, wherein in step S4, a DC component of the interference signal is extracted through a first photoelectric detector (13), the DC component is processed by a low-pass filter (12) and then transmitted to a servo controller (11), and the servo controller (11) controls a probe light generator (7) to operate at an orthogonal working point of an FPI.

14. The simultaneous detection system of claim 8, wherein in steps S4 and S5, the interference signal is received by a second photoelectric detector (14), then, the interference signal of a specific frequency is extracted by the lock-in amplifier (15), and subsequently, the interference signal of the specific frequency is demultiplexed and demodulated to obtain the second harmonic of a gas photoacoustic signal, from which the concentration information of the dissolved gas is obtained.

15. The simultaneous detection system of claim 14, wherein at the same time, a broadband interference signal ranging from 20 kHz to 500 kHz is extracted in a frequency domain of an original signal by a computer (16), and frequency and intensity information of partial discharge is obtained through demultiplexing and demodulation.

* * * * *